US011684691B2

(12) United States Patent
Tillmanns et al.

(10) Patent No.: US 11,684,691 B2
(45) Date of Patent: Jun. 27, 2023

(54) PERSONAL SANITIZING DEVICE

(71) Applicant: Otter Products, LLC, Fort Collins, CO (US)

(72) Inventors: Todd D. Tillmanns, Germantown, TN (US); Matthew M. Glanzer, Fort Collins, CO (US)

(*) Notice: Subject to any disclaimer, the term of this patent is extended or adjusted under 35 U.S.C. 154(b) by 269 days.

(21) Appl. No.: 17/229,989

(22) Filed: Apr. 14, 2021

(65) Prior Publication Data

US 2021/0322620 A1 Oct. 21, 2021

Related U.S. Application Data

(60) Provisional application No. 63/011,696, filed on Apr. 17, 2020.

(51) Int. Cl.
*A61L 9/20* (2006.01)
*G02C 5/00* (2006.01)
*A42B 1/017* (2021.01)

(52) U.S. Cl.
CPC ............... *A61L 9/20* (2013.01); *A42B 1/017* (2021.01); *G02C 5/001* (2013.01); *A61L 2209/15* (2013.01)

(58) Field of Classification Search
CPC ....... A61L 2209/15; A61L 9/20; G02C 5/001; A42B 1/017
See application file for complete search history.

(56) References Cited

U.S. PATENT DOCUMENTS

| | | | |
|---|---|---|---|
| 2,032,101 A * | 2/1936 | Sullivan | A62B 18/003 2/9 |
| 4,146,026 A | 3/1979 | Montalvo | |
| 4,282,869 A * | 8/1981 | Zidulka | A61M 16/0633 128/200.28 |
| 5,200,156 A | 4/1993 | Wedekamp | |
| 5,353,605 A * | 10/1994 | Naaman | A42B 3/285 607/109 |
| 5,447,528 A * | 9/1995 | Gerardo | A42B 1/244 607/91 |
| 5,561,862 A * | 10/1996 | Flores, Sr. | A42B 3/286 2/422 |
| 5,732,695 A | 3/1998 | Metzger | |
| 6,350,275 B1 * | 2/2002 | Vreman | A61N 5/0601 607/91 |
| 6,409,338 B1 * | 6/2002 | Jewell | G02C 11/10 351/158 |
| 6,901,930 B2 * | 6/2005 | Henley | B03C 3/12 128/205.27 |
| 7,036,502 B2 * | 5/2006 | Manne | A62B 18/003 128/200.27 |
| 7,234,831 B1 * | 6/2007 | Hanley | A42B 1/244 2/209.13 |

(Continued)

FOREIGN PATENT DOCUMENTS

WO 2017014102 A1 1/2017

*Primary Examiner* — Sean M Luck

(57) ABSTRACT

A personal sanitizing device includes an eyewear frame and one or more UV-C sources attached to a lower edge of the eyewear frame for directing UV-C energy in a downward direction from the eyewear frame. The one or more UV-C sources are configured for sanitizing air in proximity of a mouth and/or a nose of a wearer of the personal sanitizing device. The personal sanitizing device also includes a battery configured for powering the one or more UV-C sources.

9 Claims, 8 Drawing Sheets

(56) References Cited

U.S. PATENT DOCUMENTS

| | | | |
|---|---|---|---|
| 7,364,583 B2* | 4/2008 | Rose | A42B 1/244 |
| | | | 607/88 |
| 7,498,004 B2 | 3/2009 | Saccomanno | |
| 7,683,344 B2 | 3/2010 | Tribelsky et al. | |
| 7,823,586 B2* | 11/2010 | Glazman | A61L 9/20 |
| | | | 128/202.25 |
| 8,574,331 B2 | 11/2013 | Bangera et al. | |
| 8,733,356 B1* | 5/2014 | Roth | A62B 18/003 |
| | | | 128/205.27 |
| 8,960,190 B2 | 2/2015 | James et al. | |
| 9,687,575 B2 | 6/2017 | Farren | |
| 9,861,142 B1* | 1/2018 | Rebecchi | F04D 29/403 |
| 10,294,124 B2 | 5/2019 | Khan et al. | |
| 10,363,327 B2 | 7/2019 | Liao et al. | |
| 10,456,736 B2 | 10/2019 | Zhu | |
| 10,751,434 B2 | 8/2020 | Bonutti et al. | |
| 2004/0055601 A1* | 3/2004 | De Luca | A62B 18/003 |
| | | | 128/201.25 |
| 2005/0078473 A1* | 4/2005 | Zuloff | A42B 1/004 |
| | | | 362/106 |
| 2007/0133935 A1* | 6/2007 | Fine | G02B 6/0061 |
| | | | 385/131 |
| 2008/0266839 A1* | 10/2008 | Claypool | A42B 1/244 |
| | | | 2/209.13 |
| 2009/0004047 A1 | 1/2009 | Hunter et al. | |
| 2009/0294688 A1 | 12/2009 | Evans | |
| 2012/0182726 A1* | 7/2012 | King | F21S 9/037 |
| | | | 362/183 |
| 2013/0118506 A1* | 5/2013 | Osipov | A41D 13/1184 |
| | | | 128/858 |
| 2014/0102442 A1* | 4/2014 | Wilson | F24F 9/00 |
| | | | 128/200.28 |
| 2014/0268683 A1* | 9/2014 | Waters | A42B 1/244 |
| | | | 362/106 |
| 2015/0092972 A1* | 4/2015 | Lai | H04R 1/1083 |
| | | | 381/333 |
| 2015/0209597 A1* | 7/2015 | Haarlander | A61H 23/02 |
| | | | 607/90 |
| 2015/0284266 A1 | 10/2015 | Matsui | |
| 2016/0310758 A1* | 10/2016 | Friedman | A61N 5/062 |
| 2018/0264161 A1* | 9/2018 | Welch | A41D 13/1192 |
| 2019/0099613 A1* | 4/2019 | Estes | A61N 5/0616 |
| 2021/0049894 A1 | 2/2021 | Bolling et al. | |

* cited by examiner

PERSONAL SANITIZING DEVICE

CROSS REFERENCE TO RELATED APPLICATIONS

This application claims priority to U.S. Provisional Patent Application No. 63/011,696, filed Apr. 17, 2020, which is hereby incorporated by reference in its entirety.

FIELD

This application relates to the fields of personal and/or wearable sanitizing or sanitation devices for protecting against bacteria and/or viruses.

BACKGROUND

Despite advances in medical technology, various types of bacteria and viruses still cause many illnesses and deaths around the world. Many of these illnesses are contracted by breathing in airborne particles or droplets that contain the bacteria or virus. In other cases, they make contact with the face and are eventually inhaled, ingested, or transferred through touching of the face. Many of these illnesses involve respiratory infections which cause millions of deaths every year and can be particularly difficult when a pandemic occurs. Facemasks are commonly used in medical environments and are also often used by the general population when there is a risk of infection. Facemasks are also used to attempt to reduce the chances that an affected person infects others in his or her proximity.

Many types and grades of facemasks are used. Examples of common facemasks include simple disposable facemasks, surgical facemasks, N95 masks, and respirators. Facemasks have a number of drawbacks. First, they are typically uncomfortable and can make the wearer hot or sweaty underneath the mask. Second, they make it difficult to hear or understand the wearer's spoken words. Third, they must be periodically cleaned, disposed of, and/or replaced. Fourth, they typically work by trapping the bacteria or virus and must be handled carefully to avoid inadvertent transfer from the mask itself. Further, depending on the situation, facemasks may present awkward or uncomfortable situations when some people wear them and others do not. Finally, there may be negative aspects or connotations associated with wearing a facemask in some situations. Improvements in personal, wearable sanitizing devices are desired.

SUMMARY

A personal and wearable sanitizing device includes an eyewear frame and one or more ultraviolet C (also referred to as UV-C or UVC) sources attached to a lower edge of the eyewear frame for directing UV-C energy in a downward direction from the eyewear frame. The one or more UV-C sources are configured for sanitizing air that is in proximity to a mouth and/or a nose of a wearer of the personal sanitizing device. The personal sanitizing device may also include a battery configured for powering the one or more UV-C sources.

In another embodiment, a personal sanitizing hat includes a bill configured for extending forward above a face of a user when the user is wearing the personal sanitizing hat. The bill includes one or more UV-C sources attached to a lower surface of the bill for directing UV-C radiation in a downward direction from the bill. The one or more UV-C sources are configured for sanitizing air in proximity of a mouth and/or a nose of a wearer of the personal sanitizing hat. The personal sanitizing hat also includes an electrical cable and a battery for powering the one or more UV-C sources through the electrical cable.

In yet another embodiment, a wearable, personal sanitizing device includes one or more earpieces and an arm extending from each of the one or more earpieces. Each arm is configured to extend to an area near the nose and/or a mouth a user of the personal sanitizing device when the one or more earpieces are worn by the user. The one or more UV-C sources are attached to an end of each arm, the UV-C sources configured for directing UV-C energy toward the mouth and/or the nose of the user of the personal sanitizing device. The personal sanitizing device may also include a battery configured for powering the one or more UV-C sources.

BRIEF DESCRIPTIONS OF DRAWINGS

In the drawings, FIG. 1A illustrates a personal sanitizing device.

DETAILED DESCRIPTION

Ultraviolet (UV) light refers to the region of the electromagnetic spectrum between visible light and X-rays. UV light is typically referred to as light having a wavelength falling between 10 and 400 nanometers (nm). UV light is not visible to the human eye because it has a shorter wavelength and higher frequency than the light human eyes and/or brains perceive as visible. UV light is typically categorized into several different subtypes. UV-A light (320-400 nm) is UV light with the longest wavelength, and the least harmful to humans. It is more commonly known as "black light." It is often used to cause objects to emit fluorescence (a colored glowing effect) in artistic and celebratory designs. Many insects and birds can perceive this type of UV radiation visually, along with some humans in rare cases, such as in cases of Aphakia (missing optic lens). UV-B light (290-320 nm) causes sunburns with prolonged exposure along with increasing the risk of skin cancer and other cellular damage. About 95% of all UV-B light is absorbed by the ozone in Earth's atmosphere. UV-C light (100-290 nm) is almost completely absorbed by Earth's atmosphere. When studying light passing through outer space, scientists often use a different set of UV subtypes dealing with astronomical objects. The first three are similar to the categorization most commonly used in Earth sciences: Near Ultraviolet (NUV) light (300-400 nm), Middle Ultraviolet (MUV) light (200-300 nm), and Far Ultraviolet (FUV) light (100-200 nm).

The germicidal effect of UV light on bacteria and viruses is primarily due to the formation of thymine, thymine-cytosine (pyrimidine), and cytosine dimers in DNA. UV radiation with wavelengths in the range of 200-295 nm, sometimes referred to as the bactericide or germicide range, has been found to be very effective for sanitizing. UV-C light is commonly used as a disinfectant for food, air, and/or water to kill microorganisms by destroying nucleic acids in cells. It is sometimes used for treating surfaces, rooms, equipment surfaces, water, and air flowing through a duct or channel. UV-C is generally understood to be safer for human exposure than other ranges of UV light. The absorption length of UV-C radiation in human skin is extremely short such that almost no UV-C radiation can reach the living cells in the skin. In other words, most or all of the absorption occurs in the dead cell layers. In some cases, wavelengths in the specific range of 200-210 nm have been found to be very effective in these applications. In particular, some tests have found 207 nm UV light to be very effective in these applications.

Figure 1A:
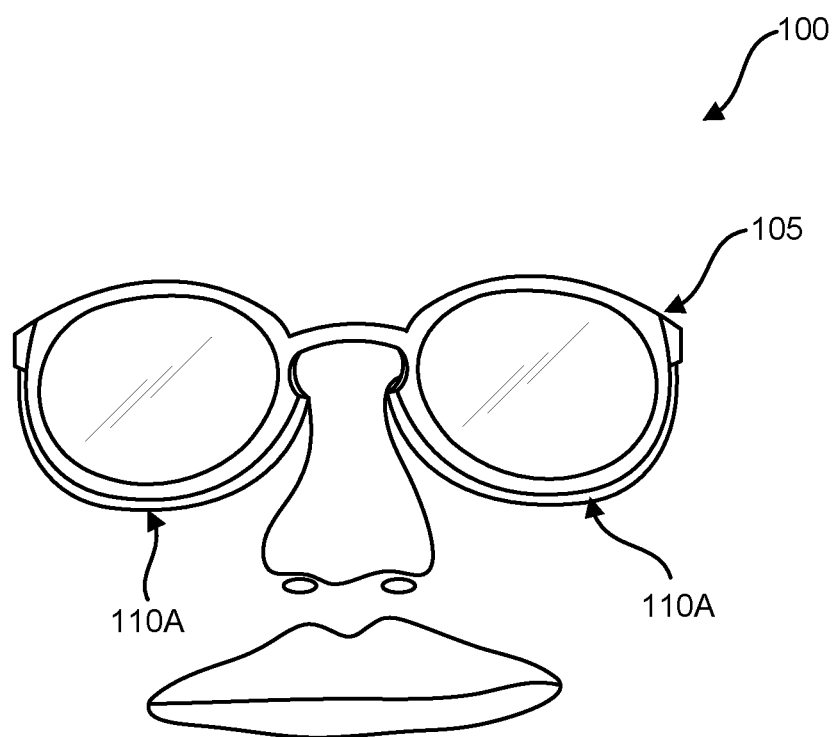
FIG. 1B illustrates components of a personal sanitizing device.

FIG. 1A illustrates a personal sanitizing device 100 that is wearable by a user. Personal sanitizing device 100 includes glasses 105 which may or may not include lenses. In some cases, personal sanitizing device 100 may be implemented with the user's existing glasses, frame, or eyewear, whether the eyewear is for vision correction, protection, or otherwise. In other examples, personal sanitizing device 100 may be implemented with a dedicated, customized, or application-specific set of eyewear or glasses. In yet other examples, personal sanitizing device 100 may be implemented on a pair of smart glasses, such as GOOGLE GLASS. While this example illustrates the sanitizing features installed on glasses 105, attachment to glasses is not necessary and the sanitizing elements may be attached to another personal item, or to no item at all.

Personal sanitizing device 100 includes UV-C arrays 110A attached to lower edges or surfaces of glasses 105. While two UV-C arrays 110A are illustrated, personal sanitizing device 100 may be implemented with any number of UV-C arrays. UV-C arrays 110A are positioned to direct UV-C light having a preferred wavelength in a generally downward direction toward the wearer's mouth and/or nose. Beneficially, the UV-C light generated by UV-C arrays 110A partially and/or fully sanitizes air inhaled and/or exhaled by the wearer, along with droplets or particles that are in the air. This allows the wearer to both reduce the risk of contracting an infection from inhaling, as well as reduce the risk of transmitting an infection to others through exhale. In addition, UV-C arrays 110A may also sanitize skin on the face around the nose and mouth. UV-C arrays 110A may be removably attached to glasses 105 or may be permanently attached to glasses 105.

While some existing masks may use UV light to sanitize inhaled and/or exhaled air, they often do so by routing air through a channel, tunnel, passageway, or other enclosed path in the mask to be treated by the UV light. Unfortunately, while these masks may realize some beneficial use of the UV light, these types of masks have some or all of the downfalls of masks discussed above. Personal sanitizing device 100 permits the personal sanitizing function to be performed without the uncomfortable, obtrusive, and unpleasant visual or aesthetic aspects of traditional masks. Personal sanitizing device 100 performs the sanitizing function in an 'open air' fashion without having to cover the wearer's nose or mouth with anything. Personal sanitizing device 100 sanitizes inhaled air and/or exhaled air without covering the nose or mouth and without having to route the air through any device, mask, filter, fabric, or membrane.

The benefits of personal sanitizing device 100 also make it more likely that a user will wear personal sanitizing device 100 a larger percentage of the time and in a greater variety of situations than a traditional mask. Consequently, both the wearer and others in proximity to the wearer are better protected. Personal sanitizing device 100 may be used as a continuous use sanitizing tool, as opposed to masks which are often only used at the greatest time of risk because of their obtrusive characteristics.

Figure 1B:
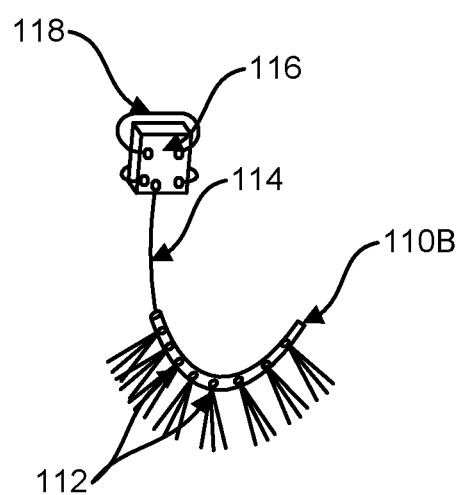

FIG. 1B illustrates some elements of a personal sanitizing device, such as personal sanitizing device 100. UV-C array 110B is an example of UV-C array 110A of FIG. 1A. Each UV-C array may include a plurality of individual UV-C light sources, such as UV-C sources 112. Any number of discrete or grouped UV-C sources may be used. In some examples, each UV-C source 112 may be a UV light emitting diode (LED) designed to transmit energy in the UV-C range, or in a subset of the UV-C range. Other types of optical or UV sources may be used. UV-C array 110B may be connected to eyewear frames, as in FIG. 1, or to one or more other items.

UV-C array 110B is connected to a battery 116, directly or indirectly, with a cable 114. Cable 114 may be any type of cable with one or more electrical conductors. UV-C array 110B may be individually connected to battery 116 or may be serially or daisy-chain connected through other devices. In some examples, UV-C array 110A or 110B may be powered by its own integrated battery or battery pack. Battery 116 may comprise one or more of a variety of electrical power storage technologies including lithium ion (Li-ion), lithium ion polymer (Li-ion polymer), lead-acid, nickel cadmium (NiCd), nickel metal hydride (NiMH), nickel-zinc, alkaline, fuel cells, lithium titanate cells, capacitive energy storage devices, super capacitors, and/or any other type of device for storing energy. While the term "battery" is primarily used herein for purposes of explanation, the apparatuses, methods, systems, and techniques described herein are applicable for use with any power or energy storage technology.

While not visible in the figures, the disclosed sanitizing devices may also contain a number of other components such as a printed circuit board, a switch, electrical components, electromechanical components, discrete components, electrical circuitry, analog components, digital components, a microprocessor, a microcontroller, memory, a voltage controller, a voltage booster, a current limiter, a battery charge controller, a battery monitor, electromechanical connectors, an electrical coil, an inductive electrical coil, a modulator, a demodulator, an rf transmitter, an rf receiver, an antenna, a filter, a mixer, and/or an amplifier. Personal sanitizing device 100 may be configured for wirelessly transmitting and/or receiving data or electronic communications from one or more other devices, such as, for example, from a smartphone over a BLUETOOTH connection. In some examples, any of the devices disclosed herein may be controlled or monitored using a software application (an app) which runs on a mobile phone, tablet, or computer.

The disclosed sanitizing devices may also include one or more display element(s) for visually conveying status or information to a user. The display element may include one or more of: a light emitting diode (LED), an organic light emitting diode (OLED), a liquid crystal display (LCD), electronic paper, electrophoretic ink, and/or another type of device for visually conveying information to a user, including combinations thereof. Display element(s) may be made up of a group of discrete display elements, such as a group of LEDs. Display element(s) may also be made up of a single display device, such as an LCD, containing a plurality of display elements, segments, or areas. Display elements(s) may be illuminated in a variety of combinations, sequences, colors, patterns, and/or intensities to convey various information about an operating mode, status, and/or condition. Any of the devices may also convey information using an audio device for generating an audible signal which may include a speaker, a buzzer, a beeper, a piezoelectric device, and/or a combination thereof. Finally, they may also include one or more buttons, switches, optical detectors, touch sensitive devices, capacitance sensors, or other devices through which a user may provide an input to the device.

The personal sanitizing devices disclosed herein may also include a strap 118. Strap 118 may be used to hold removably attach battery 116 to the user, the user's clothing, and/or to another object. Other methods of attachment may also be used including a snap, a fastener, an elastic band, hook and loop fasteners, and/or a temporary adhesive.

In some examples, any of the UV-C arrays disclosed herein may be operable at different power levels where a tradeoff may be made between sanitizing power and battery life. In other examples, personal sanitizing device 100 may operate one or more UV-C arrays in a pulsed manner or according to a designated duty cycle.

In yet other examples, a personal sanitizing device may include sensors for determining when and/or at what power levels the UV-C arrays are operated. In one example, a motion sensor or camera may be included to determine when the wearer is moving, when the wearer is inside a building, and/or when the wearer is in proximity to others. The power level and/or operation mode of the UV-C arrays may be adjusted based on information from one or more of these sensors. In another examples, an air quality sensor may be used to determine air quality and/or an estimated number of particulates or droplets in the air. Any of these factors may be used to determine when and/or at what power levels the UV-C arrays are operated.

Figure 2A:
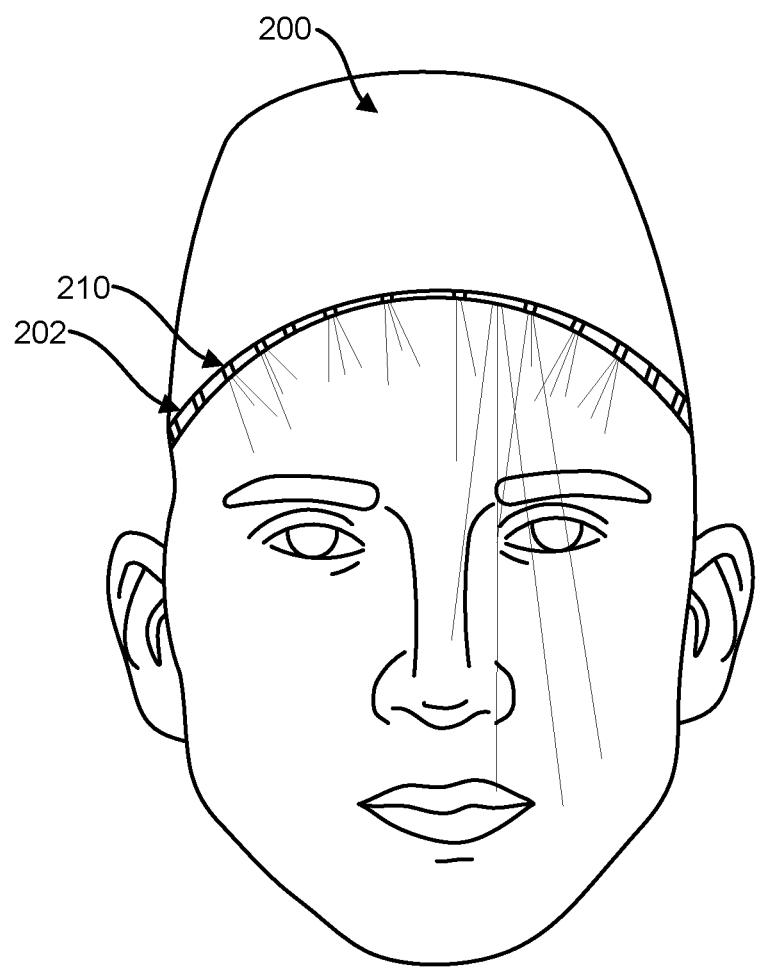
FIG. 2A illustrates a front view of an alternate embodiment of a personal sanitizing device.

FIG. 2A illustrates a front view of a personal sanitizing hat 200. Personal sanitizing hat 200 is worn by a user and performs any or all of the functions of personal sanitizing device 100 described above. Personal sanitizing hat 200 includes a bill 202 which extends over and above the wearer's face. Bill 202 includes two or more UV-C arrays 210 attached to the lower surface or undersurface. UV-C arrays 210 are examples of UV-C arrays 110A and/or 110B and may include any of the elements, features, functions, and/or components of UV-C arrays 110A and/or 110B. UV-C arrays 210 direct UV-C light downward over the face of the wearer to perform any or all of the sanitizing functions described with respect to personal sanitizing device 100. Although not illustrated in FIG. 2A, personal sanitizing hat 200 may include cable 114, battery 116, and/or any of the other components described with respect to personal sanitizing device 100. Personal sanitizing hat 200 may also be implemented as a visor or headband without fully covering the head of the user.

Beneficially, the UV-C light generated by UV-C arrays 210 partially or fully sanitize air inhaled or exhaled by the wearer, along with droplets or particles in the air. This allows the wearer to both reduce the risk of contracting an infection from inhaling as well as reduce the risk of transmitting an infection to others through exhale. In addition, UV-C arrays 210 may also sanitize skin on the face around the nose and mouth. While some existing masks may use UV light to sanitize inhaled and/or exhaled air, they often do so by routing air through a channel, tunnel, or path in the mask to be treated by the UV light. Unfortunately, while these masks may get some beneficial use of the UV light, these types of masks have some or all of the downfalls of masks discussed above. Personal sanitizing hat 200 permits the personal sanitizing function to be performed with the uncomfortable, obtrusive, or unpleasant visual or aesthetic aspects of traditional masks. Personal sanitizing hat 200 performs the sanitizing function in an 'open air' fashion without having to cover the wearer's nose or mouth. Personal sanitizing hat 200 sanitizes inhaled air and/or exhaled air without covering the nose and/or mouth and without having to route the air through any device, mask, filter, or membrane.

Further, any of the personal sanitizing devices disclosed herein may also be used for sanitizing other items. For example, bill 210 of personal sanitizing hat 200 may be placed over another item for purposes of sanitizing that item when it is not being worn by a user. For example, it may be placed over a mobile phone for purposes of sanitizing the mobile phone. Other applications are possible.

Figure 2B:
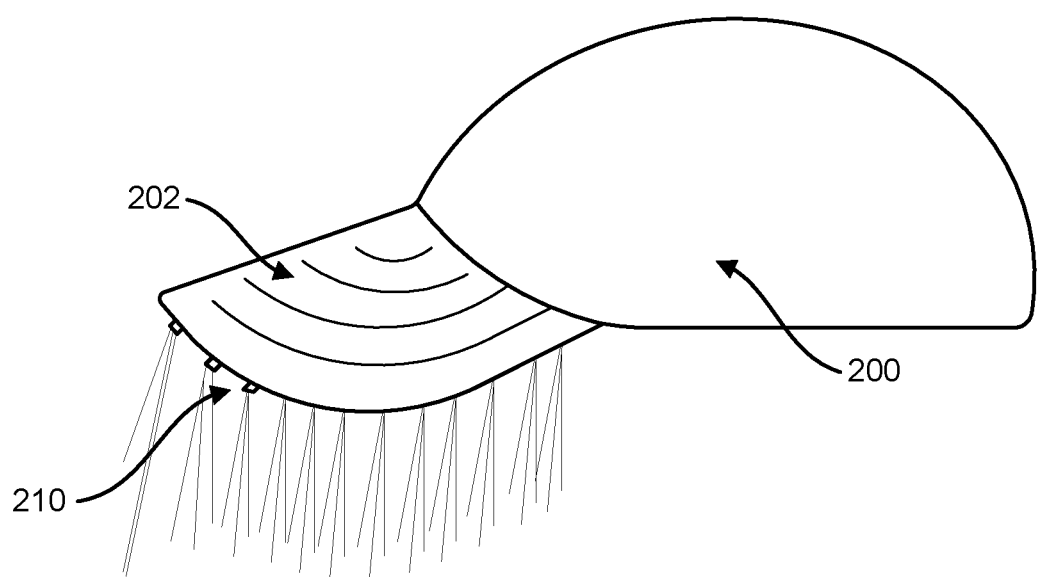
FIG. 2B illustrates a side view of the personal sanitizing device of FIG. 2A.
Figure 2C:
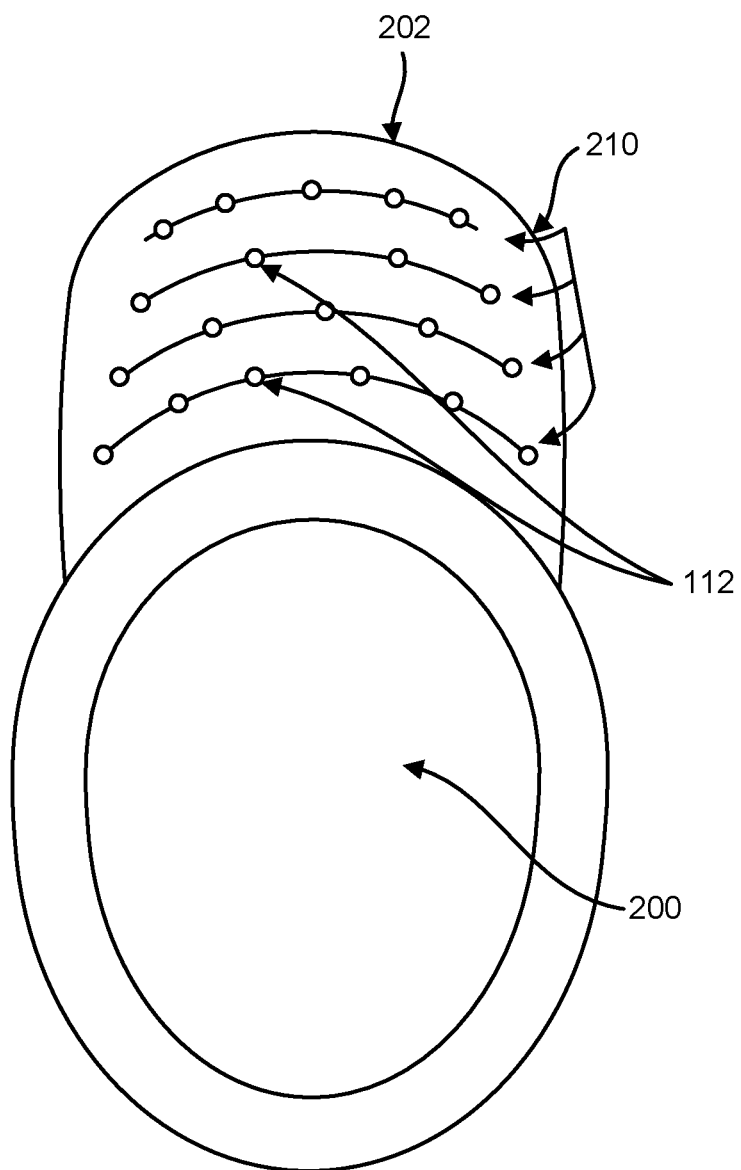
FIG. 2C illustrates a bottom view of the personal sanitizing device of FIG. 2A.

FIG. 2B illustrates a side view of personal sanitizing hat 200 of FIG. 2A. FIG. 2C illustrates a bottom view of personal sanitizing hat 200 of FIG. 2A.

In some situations, there may be a desire to reduce the amount of UV-C exposure to the user's skin, particularly if the device is going to be worn for long periods of time. A blocking lotion or creme may be applied topically to the areas of concern to reduce the amount of UV-C radiation reaching the skin. A broad-spectrum blocker may be used or a specialized blocker may be used which is formulated to be specifically effective at the UV-C wavelengths used by the device.

Figure 3A:
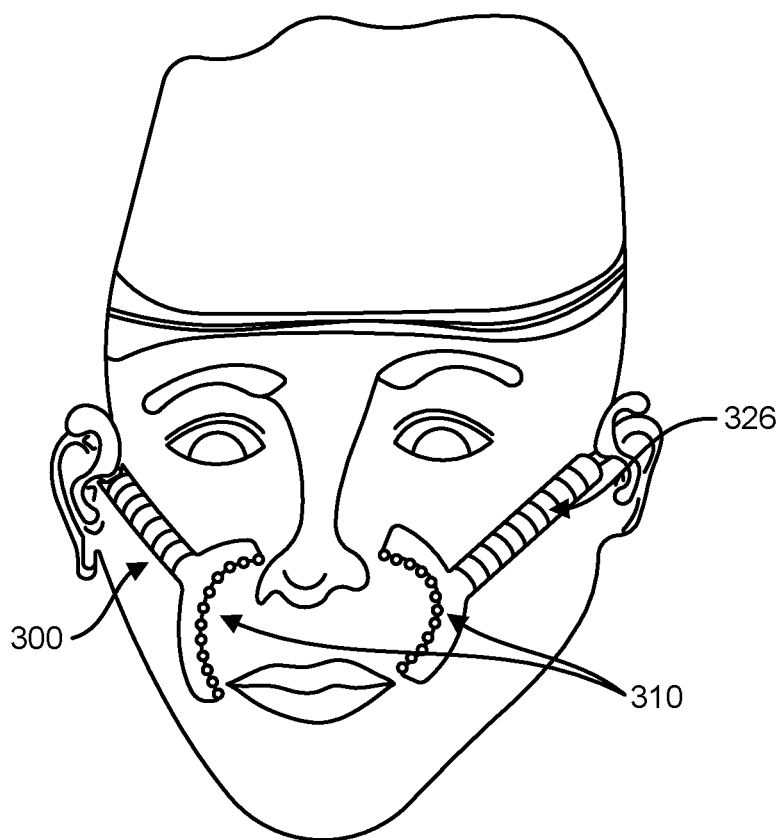
FIG. 3A illustrates an alternate embodiment of a personal sanitizing device.
Figure 3B:
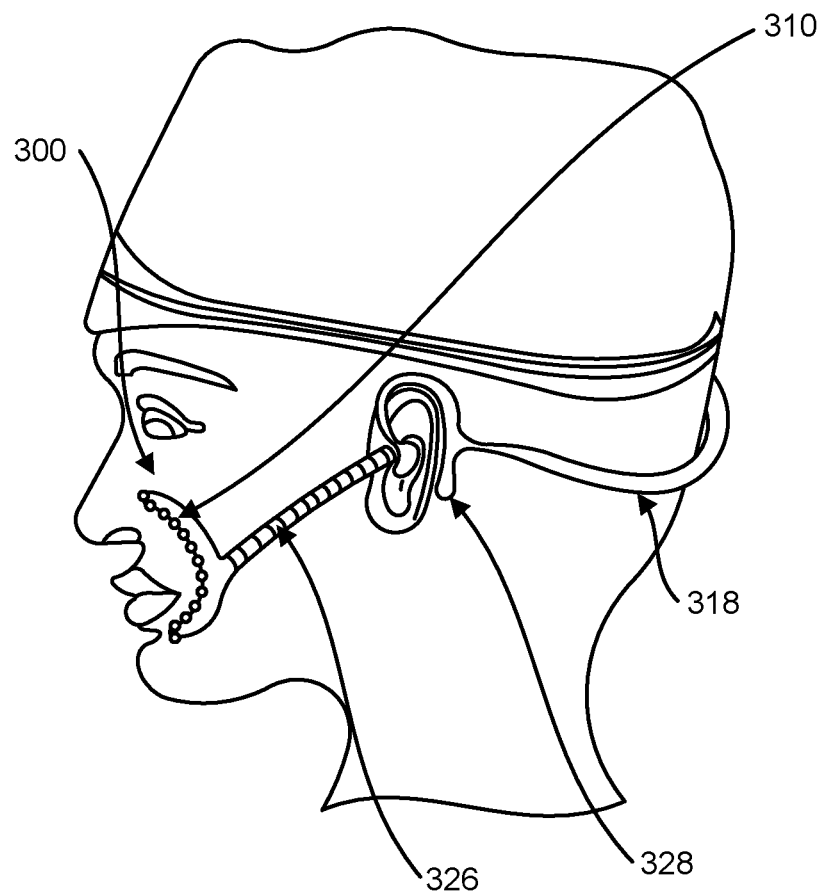
FIG. 3B illustrates a side view of personal sanitizing device of FIG. 3A.

FIG. 3 illustrates an alternate implementation of a personal sanitizing device 300 being worn by a user. Personal sanitizing device 300 performs any or all of the functions of personal sanitizing device 100 and/or personal sanitizing hat 200 discussed above. Personal sanitizing device 300 includes two arms 326 which hold UV-C arrays 310 in proximity to the nose and mouth of the wearer. UV-C arrays 310 are examples of UV-C arrays 110A, UV-C array 110B, and/or UV-C arrays 210 and may include any of the elements, features, functions, and/or components of UV-C arrays 110, UV-C array 110B, and/or UV-C arrays 210. UV-C arrays 310 direct UV-C light directly toward the mouth and nose area of the wearer to perform any or all of the sanitizing functions described with respect to personal sanitizing device 100 and/or personal sanitizing hat 200. Arms 326 may also include one or more UV-C sources or arrays for greater and/or more intense UV-C coverage.

Personal sanitizing device 300 also includes one or more earpieces 328 which hold arms 326 in position. As illustrated in the side view of FIG. 3B, personal sanitizing device 300 may also include a strap 318. Although personal sanitizing device 300 may not be as discrete or unobtrusive as personal sanitizing device 100 and/or personal sanitizing hat 200, the proximity to the nose and mouth area may make it more effective and, therefore, beneficial in medical and healthcare applications. Although not illustrated in FIGS. 3A and 3B, personal sanitizing device 300 may include cable 114, battery 116, and/or any of the other components of personal sanitizing device 100 and/or personal sanitizing hat 200.

Beneficially, the UV-C light generated by UV-C arrays 310 partially or fully sanitize air inhaled or exhaled by the wearer, along with droplets or particles in the air. This allows the wearer to both reduce the risk of contracting an infection from inhaling and reduce the risk of transmitting an infection to others through exhale. In addition, UV-C arrays 310 may also sanitize skin on the face around the nose and mouth. While some existing masks may use UV light to sanitize inhaled and/or exhaled air, they often do so by routing air through a channel, tunnel, or path in the mask to be treated by the UV light. Unfortunately, while these masks may get some beneficial use of the UV light, these types of masks have some or all of the downfalls of masks discussed above. Personal sanitizing device 300 permits the personal sanitizing function to be performed with the uncomfortable, obtrusive, or unpleasant visual or aesthetic aspects of traditional masks. Personal sanitizing device 300 performs the sanitizing function in an 'open air' fashion without having to cover the wearer's nose or mouth. Beneficially, personal sanitizing device 300 sanitizes inhaled air and/or exhaled air without covering the nose and/or mouth of the user and without having to route the air through any device, mask, filter, or membrane.

Figure 4:
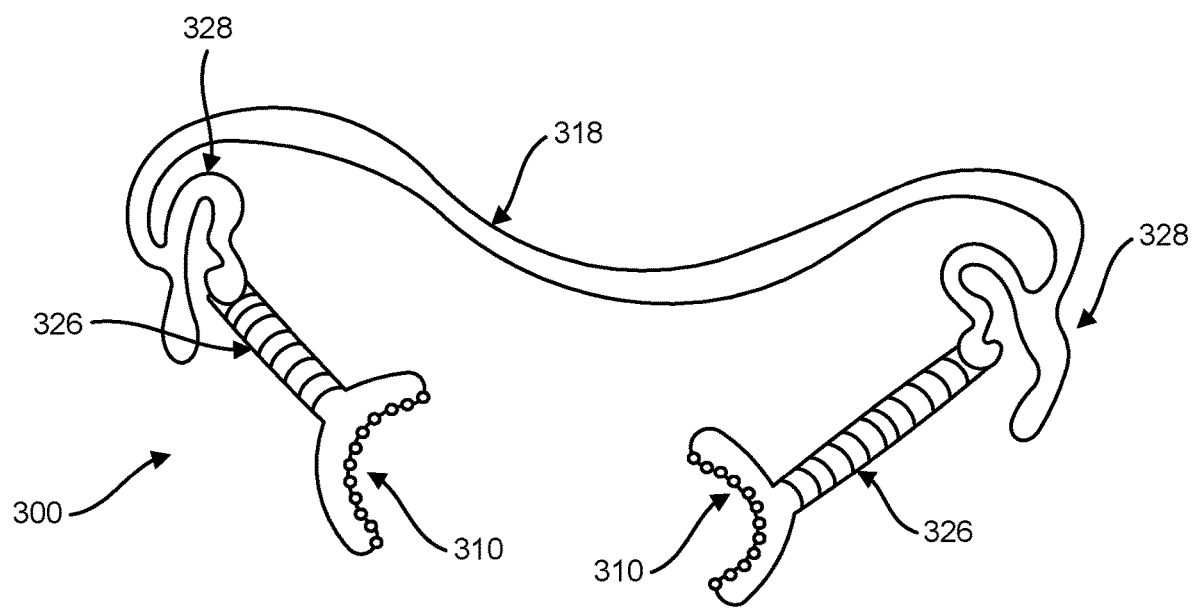
FIG. 4 illustrates another view of the personal sanitizing device of FIG. 3A.

FIG. 4 illustrates personal sanitizing device 300 when not being worn by a user. In some examples, any of the personal sanitizing devices disclosed herein may not include the battery and may include a cable to a power source when a user is not expected to be moving around very much, such as during a medical procedure. In some examples, arms 326 may be adjustable, bendable, flexible, and/or telescoping.

The apparatuses, systems, methods, techniques, and components described herein are meant to exemplify some types of possibilities. In no way should the aforementioned examples limit the scope of the invention, as they are only exemplary embodiments.

The foregoing disclosure has been presented for purposes of illustration and description. Other modifications and variations may be possible in view of the above teachings. The examples described in the foregoing disclosure were chosen to explain the principles of the concept and its practical application to enable others skilled in the art to best utilize the invention. It is intended that the claims be construed to include other alternative embodiments of the invention except as limited by the prior art.

The phrases "in some embodiments," "according to some embodiments," "in the embodiments shown," "in other embodiments," "in some examples," "in some cases," "in some situations," "in one configuration," "in another configuration," and the like generally mean that the particular feature, structure, or characteristic following the phrase is included in at least one embodiment of the present invention and/or may be included in more than one embodiment of the present invention. In addition, such phrases do not necessarily refer to the same embodiments or different embodiments.

What is claimed is:

1. A personal sanitizing device comprising:
   an eyewear frame;
   one or more UV-C source modules attachable to a lower edge of the eyewear frame for directing UV-C energy in a downward direction from the eyewear frame, wherein the one or more UV-C source modules is configured for sanitizing air in proximity to a mouth and/or a nose of a wearer of the personal sanitizing device; and
   a battery pack configured for powering the one or more UV-C sources.

2. The personal sanitizing device of claim 1 wherein the personal sanitizing device is configured to not cover the nose or the mouth of the wearer in operation.

3. The personal sanitizing device of claim 1 wherein the personal sanitizing device does not include a membrane or filter.

4. The personal sanitizing device of claim 1 wherein the personal sanitizing device does not include an enclosed channel through which the air must pass for sanitization.

5. The personal sanitizing device of claim 1 wherein the one or more UV-C modules is two UV-C modules each configured to removably attach to a respective lower edge of the eyewear frame under a respective lens area of the eyewear frame.

6. The personal sanitizing device of claim 1 wherein each of the one or more UV-C modules is permanently attached to the eyewear frame.

7. The personal sanitizing device of claim 1 wherein each of the one or more UV-C modules includes a plurality of UV-C light emitting diodes.

8. The personal sanitizing device of claim 1 further including a switch for selectively activating and deactivating the one or more UV-C modules.

9. The personal sanitizing device of claim 1 further comprising a motion sensor wherein an operation mode of the UV-C modules is changed based on information received from the motion sensor.

\* \* \* \* \*